(12) United States Patent  (10) Patent No.: US 6,969,366 B1
Reddick  (45) Date of Patent: Nov. 29, 2005

(54) HANDS-FREE CHIN LIFT AND AIRWAY SUPPORT DEVICE

(76) Inventor: Joan Marie Reddick, 933 Michigan Ave., Palm Harbor, FL (US) 34683

( * ) Notice: Subject to any disclaimer, the term of this patent is extended or adjusted under 35 U.S.C. 154(b) by 0 days.

(21) Appl. No.: 10/366,761

(22) Filed: Feb. 14, 2003

(51) Int. Cl.[7] .............................................. A61F 5/00
(52) U.S. Cl. ..................................................... 602/18
(58) Field of Search ............................. 602/17, 18, 19; 128/DIG. 23

(56) References Cited

U.S. PATENT DOCUMENTS

| | | | | |
|---|---|---|---|---|
| 4,700,697 A | * | 10/1987 | Mundell | 128/DIG. 23 |
| 4,782,824 A | * | 11/1988 | Davies | 128/76 R |
| 5,632,283 A | * | 5/1997 | Carden | 128/845 |
| 6,171,314 B1 | * | 1/2001 | Rotramel | 602/18 |

* cited by examiner

*Primary Examiner*—Michael A. Brown
(74) *Attorney, Agent, or Firm*—Swidler Berlin LLP

(57) ABSTRACT

A support device (10) having a chin rest (12), malleable shaft (14), and base (16) and a method of using device to maintain patency to the airway of a person with a decreased level of consciousness. The head of the person is positioned such that airway patency is confirmed. The device is then positioned such that airway patency of the person is maintained as needed.

17 Claims, 4 Drawing Sheets

HANDS-FREE CHIN LIFT AND AIRWAY SUPPORT DEVICE

FIELD OF INVENTION

This invention relates to anesthesia delivery, specifically to an improved method for supporting the mandible to prevent airway obstruction.

BACKGROUND OF THE INVENTION

Monitored Anesthesia Care (MAC) anesthesia is the commonly used anesthetic technique consisting of delivering drugs into the bloodstream in combination with local anesthetic infiltration by the surgeon at the operative site. MAC anesthesia is often used in combination with regional anesthesia, such as spinals, epidurals, and peripheral nerve blocks, which also provide temporary loss of feeling and movement at the operative site. The risk of using MAC anesthesia is that upper airway obstruction may occur due to respiratory depression.

During surgery, respiratory depression can occur in any person whose level of consciousness is decreased due to sedation from MAC anesthesia. Respiratory depression in the unconscious person is the result of the loss of tonicity of the submandibular muscles, which provide direct support of the tongue and indirect support to the epiglottis. As a result of this loss of tonicity, posterior displacement of the tongue may occlude the airway at the level of the pharynx, and the epiglottis may occlude the airway at the level of the larynx. The basic technique for opening the airway is the head-tilt with anterior displacement of the mandible (chin-lift or jaw-thrust maneuver).

Thus, to prevent airway obstruction, the anesthetist must achieve proper airway positioning in the patient to maintain airway patency. To this end, the anesthetist will first attempt the chin lift maneuver, which consists of manually lifting the chin upwards. This maneuver provides maintenance of proper head tilt and anterior displacement of the mandible resulting in proper alignment of the airway structures, which contributes to patient air exchange. Another option is the jaw-thrust maneuver, which is performed by placing one's hands at both sides of the mandible laterally and thrusting the jaw forward. Both methods require the anesthetist to support the patient's head manually throughout the duration of the surgery.

In some MAC anesthesia cases, an oropharyngeal or nasopharyngeal airway may be necessary to maintain airway patency. An oropharyngeal airway is a plastic, disposable, semi-circular shaped device that, when in proper position, will hold the tongue away from the posterior wall of the pharynx. However, even with the use of this device, proper head position must be maintained using either the chin-lift or jaw-thrust maneuver to keep the airway patent. indicated when the insertion of the oral airway is technically difficult or if the oral airway provides only partial relief of the airway obstruction. The airway is lubricated with a water-soluble lubricant and gently inserted close to the midline along the floor of the nostril into the posterior pharynx behind the tongue. Again, it is important to maintain head-tilt with anterior displacement of the mandible by chin-lift and, if necessary, jaw thrust when using the oropharyngeal or nasopharyngeal airway.

Surgical procedures using MAC anesthesia can range from fifteen minutes to as long as two hours. The anesthetist must continuously administer sedative medications and, assess patient response to those medications, as well as monitor and document vital signs on the patient's chart. If the anesthetist must physically perform the chin lift maneuver throughout the duration of the procedure in order to maintain patency of the airway, the additional responsibilities of monitoring, documentation, and medication administration become more cumbersome. Additionally, other factors, such as the position of the patient, often make the performance of the chin-lift maneuver awkward and inhibit the anesthetist from performing his/her other responsibilities.

In some cases, when it is obvious that maintaining continuous pressure on the mandible will be too taxing upon the anesthesia provider, he or she will choose to use general anesthesia instead of MAC anesthesia to anesthetize the patient. General anesthesia carries the risk of major complications including death, myocardial infarction, and stroke, and it also is associated with less serious complications such as vomiting, sore throat, headache, shivering, and delayed return to normal mental functioning. Thus, the disadvantages of the current methods of manually preventing airway obstruction and maintaining airway patency include:

(a) The anesthetist's movement may be restricted as a result of maintaining contact with the patient's mandible at all (b) The anesthetist is impeded in the task of performing his or her other tasks, such as delivering medications and charting vital signs during surgery as a result of being forced to maintain continuous physical contact with the patient's mandible at all time. This results in a less efficient and more laborious performance of additional responsibilities.

(c) Factors such as operating room table placement and patient positioning can make it difficult to maintain constant upward pressure on the chin during long procedures.

(d) The anesthetist may become unnecessarily fatigued and/or stiff as a result of laboriously maintaining constant pressure upon the patient's chin.

(e) If the process of maintaining the proper head position during a MAC case becomes too laborious due to the aforementioned reasons, the anesthesia provider may choose to induce general anesthesia to alleviate these difficulties, which results in increased risk to the patient such as sore throat, increased nausea, and injury to teeth.

OBJECTS AND ADVANTAGES

With the "Hands-Free Chin Lift and Airway Support Device," the anesthetist will more efficiently provide patient care during MAC anesthesia, as this device makes it unnecessary for the anesthetist to continuously perform the chin-lift maneuver manually. Accordingly, several objects and advantages of the present invention are:

(a) to prevent the impediment of the anesthetist's being forced to maintain continuous physical contact with the patient's mandible at all times.

(b) to allow the anesthetist unrestricted movement around the patient bed (c) to facilitate the anesthetist in performing his or her tasks, such as delivering medications and charting vital signs during surgery.

(d) to render unimportant those factors such as operating room table placement and patient positioning in maintaining constant upward pressure on the chin during long procedures.

(e) to prevent the anesthetist from becoming unnecessarily fatigued and/or stiff as a result of laboriously maintaining constant pressure upon the patient's chin.
(f) to prevent the anesthesia provider from being forced to induce general anesthesia in the patients to alleviate the difficulties to him/herself, which results in decreased risk of complications such as sore throat, increased nausea, and injury to teeth.
(g) to provide stable, constant chin-lift support in all patients who undergo MAC anesthesia
(h) to provide a sterile, disposable method for hands-free support of the mandible allowing proper alignment of anatomical structures of the airway, resulting in optimal air exchange, thereby preventing and/or resolving obstruction.

Further objects and advantages are to provide a device which can be used easily and safely, and which is simple to use and inexpensive to manufacture. Still further objects and advantage will become apparent from a consideration of the ensuring description and drawings.

SUMMARY

The present invention is a hands free chin lift and airway support device. It is designed to provide support for the head of a patient when the muscles supporting the head are in a state of relaxation due to anesthesia delivered during a medical procedure. In its preferred embodiment, the device will have a chin rest that conforms to the anatomy of a patient's mandible so the patient's head position remains constant during movements that may occur during a medical procedure. The shaft of the device in the preferred embodiment will consist of a material that will be flexible and malleable and will retain shape when adjusted by the user of the device. The shaft of the device will transfer the weight of a patient's head to the base. The base in the preferred embodiment will be anchored to the patient's chest both by adhesive and by the friction caused by the transfer of force from the patient's head.

DRAWINGS—FIGURES

DRAWINGS—REFERENCE NUMERALS

Figure 1A:
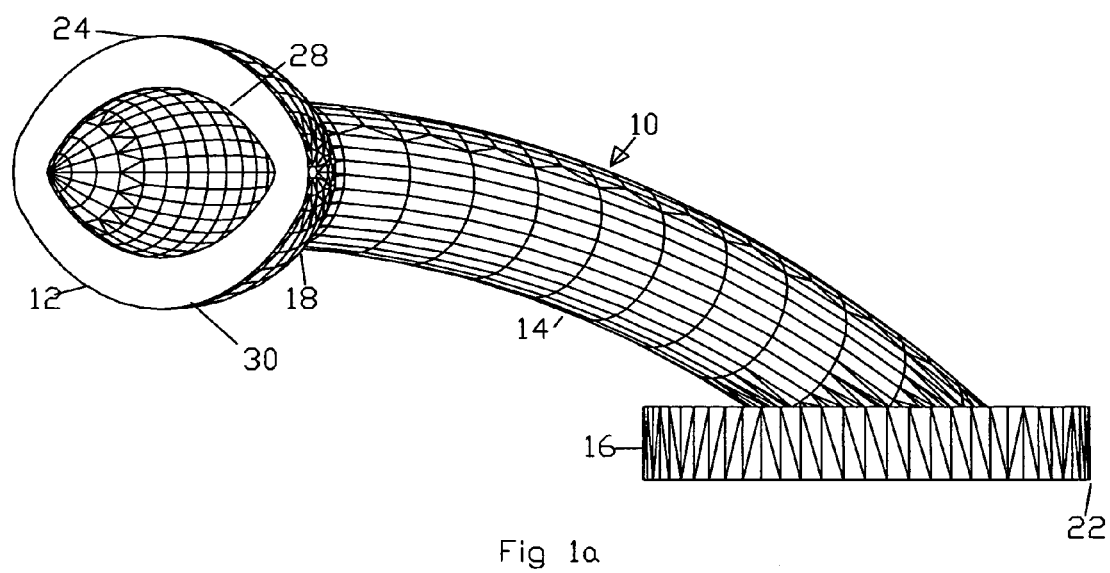
FIG. 1a is a perspective view of the hands free chin lift and airway support device shown with the shaft shown bent at the anticipated use angle.

| 10 | chin lift and airway support device |
|---|---|
| 12 | chin rest |
| 14 | central shaft |
| 16 | base |
| 18 | point where chin rest attaches to base |

-continued

| 20a | flared end of shaft |
|---|---|
| 20b | flared end of shaft |
| 22 | distal end of device |
| 24 | proximal end of device |
| 26 | adhesive |
| 28 | inner ellipse of chin rest |
| 30 | outer ellipse of chin rest |
| 32a | base of alternative embodiment |
| 32b | base of alternative embodiment |
| 34a | shaft of alternative embodiment |
| 34b | shaft of alternative embodiment |
| 36 | chin rest of alternative embodiment |
| 38 | patient's manubrium |
| 40 | head in sniffing position |

DETAILED DESCRIPTION—FIGS. 1A, 1B, 1C, AND 2—PREFERRED EMBODIMENT

Referring to the drawings wherein like numerals represent like parts throughout the several views, there is generally disclosed at 10 a hands free chin lift and airway support device. The hands free chin lift and airway support device herein referred to as device consists of three main components: the chinrest, the shaft, and the base. In the preferred embodiments the components are made of a flexible thermoplastic elastomer such as polyethyleneterephthalate, available from Atofina Chemical, Inc. of Philadelphia, Pa. However, the components may consist of any other material that can be repeatedly bent and that can hold its bent shape without fracturing, such as polyethylene, polypropylene, vinyl, nylon, rubber, leather, various impregnated or laminated fibrous materials, various plasticized materials, cardboard, paper, etc.

Figure 1B:
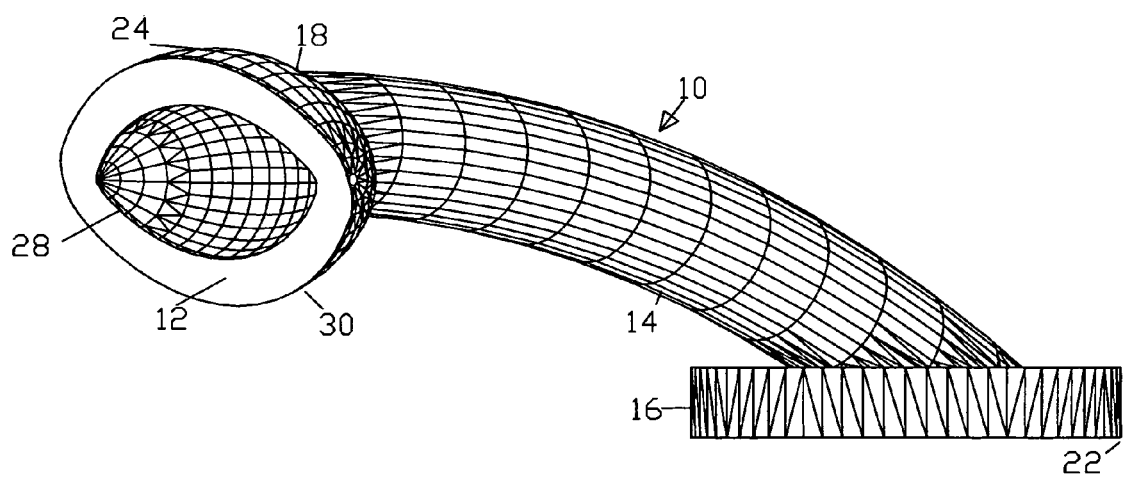
FIG. 1b is a perspective view of the hands free chin lift and airway support device with the chin rest bend downward.
Figure 1C:
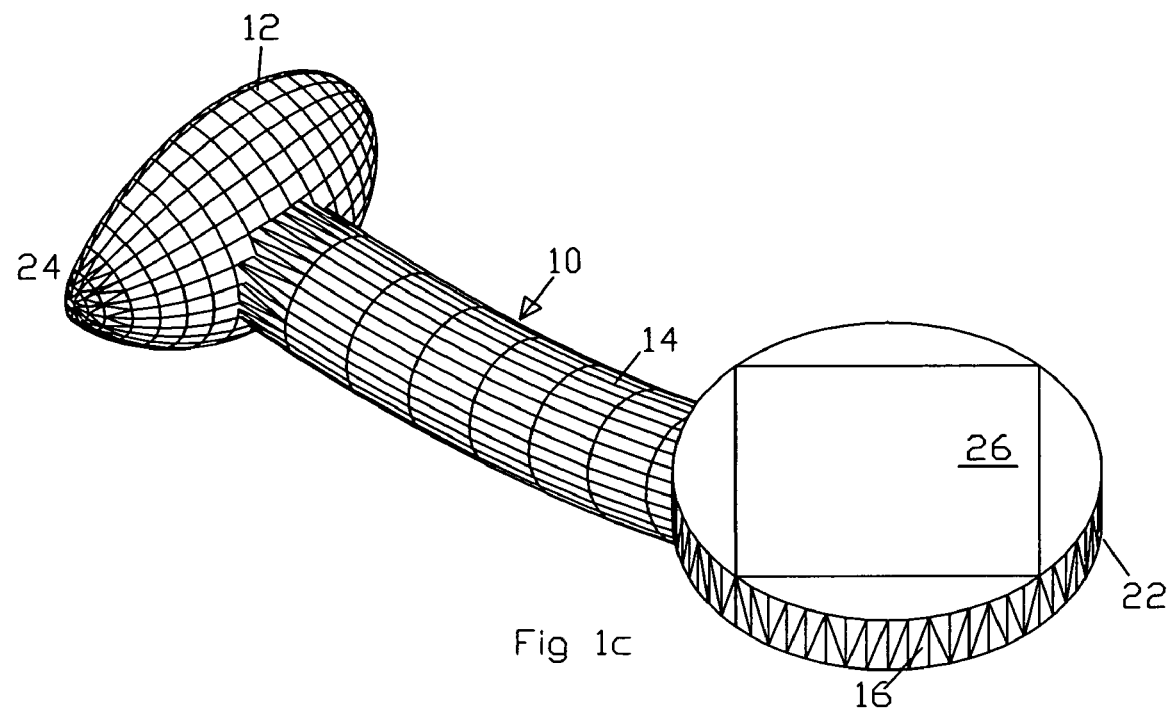
FIG. 1c is a perspective view of the bottom of the hands free chin lift and airway support device.

Perspective views of a hands free chin lift and airway support device are shown in FIGS. 1a–1b. In the FIG. 1a embodiment of the present invention, one end of the device, referred to as proximal end 24, is the chin rest 12. The chin rest is connected to a central shaft 14 which is connected to a base 16. The chin rest 12 comprises a material that will provide the user with the flexibility to mold the chin rest to fit the shape of the mandible of a patient. When in place, the chin rest will hold shape throughout the medical procedure such that the device will not slip from the chin. In an embodiment of the present invention, the lower portion 30 of the chin rest 12 is ellipsoidal in shape. The shape of the chin rest 12 is best described as like that of a pitted and halved avocado. This unique shape allows support on both sides of a patient's mandible while encompassing the patient's chin to prevent the head from sliding out of a desired position 40. The chin rest 12 is connected to the base 16 of the device by virtue of extrusion of liquid plastic.

Figure 2:
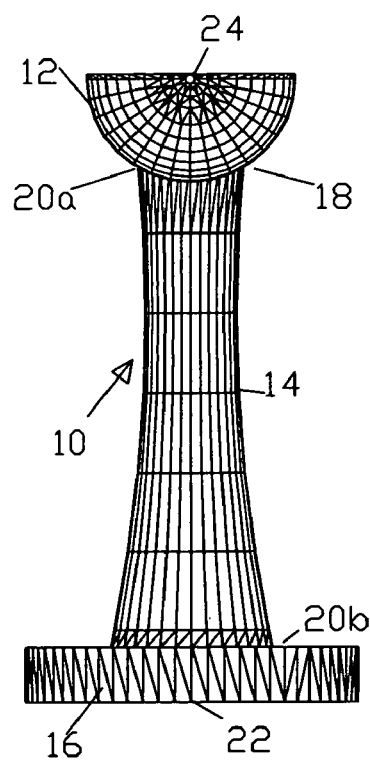
FIG. 2 shows the device in an upright position at rest, such that no internal stress is present in the device.

At the point of contiguity 18 of the chin rest 12 and the shaft 14, the chin rest 12 will be able to slightly bend up and down as shown in FIG. 1b. The shaft 14, in a preferred embodiment, is a cylindrical solid that is malleable in order to accommodate a patient's anatomy. A hands free chin lift and airway support device in an upright position at rest is shown in FIG. 2. In the FIG. 2 embodiment of the present invention, the shaft is flared outward at both ends 20a–20b to aid in structural integrity of the device 10. After the shaft 14 is bent, the device 10 will hold configuration throughout the procedure.

At one end of the device 10, referred to as a distal end 22, the shaft 14 will transfer the weight of a patient's head to the base 16. The shaft 14 of the device 10 is contiguous with the base and attached by virtue of extrusion of liquid plastic. The base 16 of the device is cylindrical in shape. The base 16 will hold the device in place on a patient's manubrium 38 such that the device will not move during use. This securement is achieved through the friction caused by the weight transferred from the head of the patient and through an adhesive 26 added to the bottom of the base 16.

While various sizes of the various components may be utilized, the device as shown has an overall length of 280 millimeters. The shaft of the device is 22.8 millimeters in length, and 51 millimeters in diameter. The base of the device is typically 127 millimeters in diameter and 12.7 millimeters high. The chin rest is half ellipsoid configuration with an inner 20 and outer 22 ellipses. The inner long axis is 127 millimeters, and the inner short axis is 63.5 The sizes and figures stated herein are shown for an adult device. With different dimensions the same configuration of device can be used for infant, child or adolescent and are within the scope of the present invention.

Figure 3A:
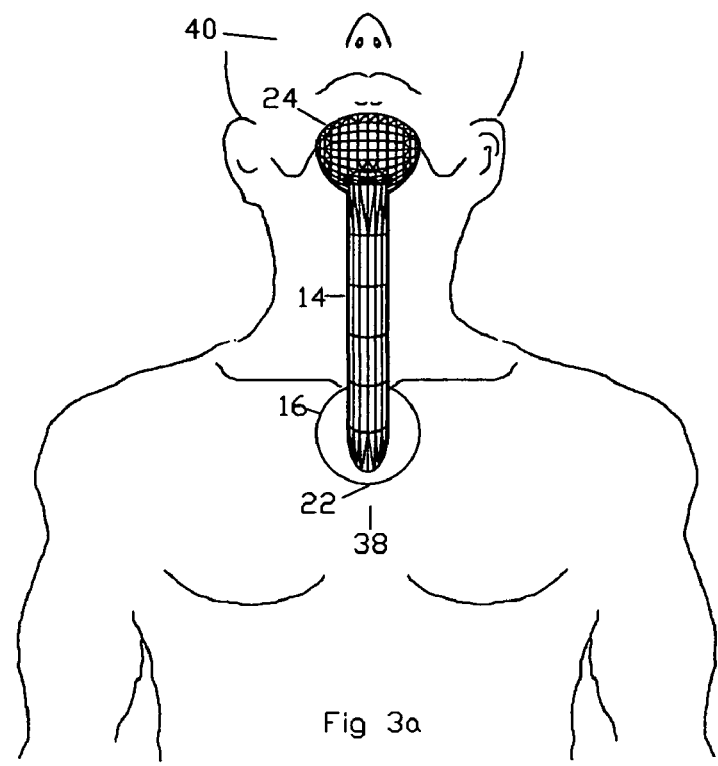
FIG. 3a shows a top view of the device in use.
Figure 3B:
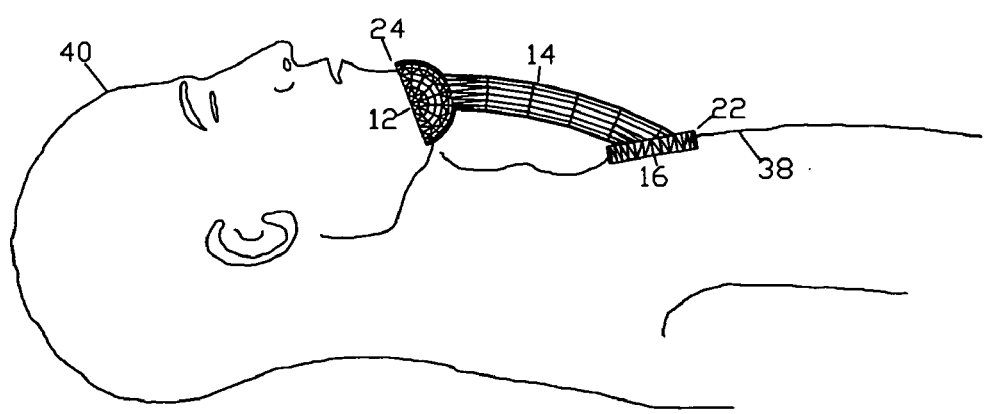
FIG. 3b shows a side view of the device in use.

Operation—FIGS. 3a–3b

In use, the distal end 22 of the device is placed approximately at the level of a patient's manubrium 38. The patient's head is positioned in the sniffing position with the mandible lifted upward such that good airway patency is confirmed by both visually observing the chest rise and fall and by feeling the patient's breath on the user's hand. The sniffing position is defined as the position of the head from neutral position rotated 90° facing front and fully abducted 40. The proximal end of the device 24 is then placed on the patient's manubrium. The device is then stabilized by adjusting the malleable shaft 14 and the chin rest 12 on the proximal end of the mandible. The airway patency is reevaluated. If a partial airway obstruction still exists, an oropharyngeal and/or nasopharyngeal is placed in the patient's esophagus, and the device is repositioned as necessary. Confirmation of airway patency is noted, and the user will then continue to maintain vigilant monitoring of the patient airway throughout the procedure.

Figure 4:
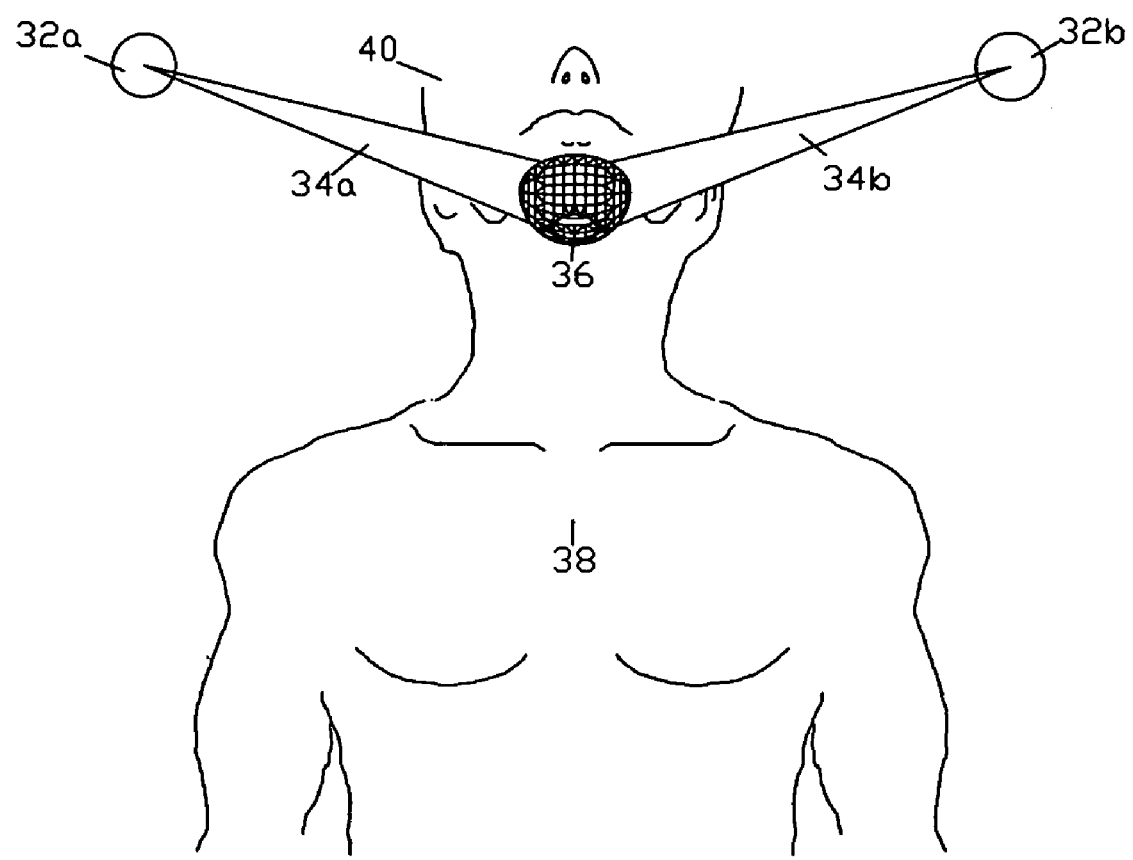
FIG. 4 shows an alternative embodiment in which the base is placed behind the head.

FIG. 4–Alternative Embodiment

An alternative embodiment will have two bases 32a and 32b. These bases may be poles, rails, hooks, etc. These bases will be positioned on both sides of and behind the patient's head. Two shafts 34a and 34b comprising of rope, tape, plastic, rubber, etc. will be attached to each base. At the midpoint of the shaft, the chinrest 36 will be placed on the patient.

Operation–FIG. 6

The operation of the alternative embodiment differs from the operation of the preferred embodiment in that the bases 32a and 32b are positioned and secured behind the patient's head. The patient's head is placed in the sniffing position, and the chin rest 12 is placed on the mandible. The shafts 34 of the device are pulled taught to maintain the position of the head as needed.

Advantages

From the description above, a number of advantages of the "Hands-Free Chin Lift and Airway Support Device" become evident:

(a) The anesthetist will not be forced to maintain continuous physical contact with the patient's mandible at all times.
(b) The anesthetist will be able to move freely as necessary as a result of not having to maintain continuous physical contact with the patient.
(c) The anesthetist will have the unimpeded ability to perform his or her other tasks, such as delivering medications and charting vital signs, during surgery as a result of not being forced to maintain continuous physical contact with the patient's mandible at all time. This results in a more efficient and less laborious performance of additional responsibilities.
(d) Factors such as operating room table placement and patient positioning will have no effect on the anesthetist's ability to maintain constant pressure on the chin during long procedures
(e) The anesthetist will not become unnecessarily fatigued and/or physically taxed as a result of laboriously maintaining constant pressure upon the patient's chin, but instead will be free to move to suit the needs of his/her body.
(f) The process of maintaining the proper head position during a MAC case will not become too laborious, so the anesthesia provider will not have to resort to inducing general anesthesia to alleviate these difficulties. Thus, the negative effects of general anesthesia, such as potential for stroke, increased nausea, and injury to teeth may be avoided.
(g) All patients undergoing MAC anesthesia will have ability to have sterile, constant chin support.
(h) The anesthetist will have the ability to provide a sterile, disposable method for hands-free support of the mandible allowing proper alignment of anatomical structures of the airway, resulting in optimal air exchange, thereby preventing and/or resolving obstruction.
(i) The device will fit a variety of patient sizes, which will allow the anesthesia provider to use the device whenever necessary.
(j) The device will be disposable, allowing the anesthesia provider to maintain sterile conditions for each patient.

CONCLUSION, RAMIFICATIONS, AND SCOPE

Accordingly, the reader will see that the "Hands-Free Chin Lift and Airway Support Device" can provide hands-free support of a person's mandible in order to allow proper alignment of anatomical structures of the airway, which will result in optimal air exchange, anesthesia provider's manually performing the chin-lift and/or jaw thrust maneuvers to maintain air patency and to prevent airway obstruction which will prevent fatigue and remove the impediments to the anesthetist's performing his/her other tasks. Further, the device has the additional advantages in that it prevents the impediment of the anesthetist's being forced to maintain continuous physical contact with the patient's mandible at all times.

it allows the anesthetist unrestricted movement around the patient bed and operating room.

it facilitates the anesthetist in performing his or her tasks, such as delivering medications and charting vital signs during surgery.

it renders unimportant those factors such as operating room table placement and patient positioning in maintaining constant upward pressure on the chin during long procedures.

it prevents the anesthetist from becoming unnecessarily fatigued and/or stiff as a result of laboriously maintaining constant pressure upon the patient's chin.

it prevents the anesthesia provider from being forced to induce general anesthesia in the patients to alleviate the difficulties to him/herself, which results in decreased risk of complications such as potential sore throat, increased nausea, and injury to teeth.

it provides stable, constant chin-lift support in all patients who undergo MAC anesthesia.

it provides a clean, disposable method for hands-free support of the mandible allowing proper alignment of anatomical structures of the airway, resulting in optimal air exchange, thereby preventing and/or resolving obstruction.

Although the description above contains many specifications, these should not be construed as limiting the scope of the invention but as merely providing illustrations of some of the presently preferred embodiments of this invention. For example, the chin rest may be made of or contain a variety of different materials, such as gel padding, foam, tape, plastic, or any other material that provides comfort and mandible stability. The central malleable shaft may come in a variety of lengths and widths so as to fit an assortment of patient sizes; it may range from a piece of hollow or solid tubing to any predetermined shape made of any malleable material which can provide rigidity and which will maintain structural integrity. Additionally, the base shape, diameter, length, or adhesive properties may be increased or decreased as necessary to anchor the base to the patient's chest. The method of device adhesion should not be limited to adhesive, but may be tape, weight, gum, putty, pressure, friction, or any method that will provide comfort and ease of use while maintaining adhesive properties. Further, the components may comprise any other material that can be repeatedly bent and hold its bent shape without fracturing, such as but not limited to polyethylene, polypropylene, vinyl, nylon, rubber, leather, various impregnated or laminated fibrous materials, various plasticized materials, cardboard, and paper. The method of connecting the chin rest, shaft, and base is not limited to liquid plastic extrusion, but may be glue or other adhesive, solder, pin and rod assembly, welding, solvent-bonding, snap-fitting, threaded assembly, or any other method whereby the chin rest and base may be permanently or temporarily attached to the shaft.

Thus, the scope of the invention should be determined by the appended claims and their legal equivalents, rather than by the examples given.

What is claimed is:

1. A system for assisting in the maintenance of patency to a patient's airway, comprising:
    a malleable shaft support portion comprising a flexible material that will maintain its shape when bent;
    a malleable chinrest support portion comprising a flexible material that includes an upper portion including a concave inner area shaped to substantially surround a portion of the patient's chin received therein, and a lower portion coupled to, and extending towards, a first end of the shaft support portion; and
    a base portion comprising a malleable material including an upper portion coupled to a second end of the shaft support portion and a lower portion configured for stable positioning on a patient's manubrium; and
    an adhesive coupled to the lower portion of the base portion having adherence to the skin at least sufficient to prevent the base portion from sliding on the patient's manubrium.

2. The system according to claim 1, wherein the shaft support portion, the chinrest support portion and base portion comprise a flexible thermoplastic elastomer planar.

3. The system according to claim 2, wherein the flexible thermoplastic elastomer is polyethyleneterephthalate.

4. The system according to claim 3, wherein the shape of the shaft support portion is one of: a cylinder, a circle, a rectangle, and a square.

5. The system according to claim 3, wherein the shape of the base portion is one of: a cylinder, a circle, a rectangle, and a square.

6. The system according to claim 1 wherein said upper base portion is attached to an end of the shaft support portion through extrusion of liquid plastic.

7. The system according to claim 1 wherein a lower portion of the chinrest support portion is attached to a first end of said shaft support portion through extrusion of liquid plastic.

8. The system according to claim 1, wherein the chinrest support portion is wider than the shaft support portion.

9. The system according to claim 1, wherein the base support portion is wider than the shaft support portion.

10. The system according to claim 1, wherein the shaft support portion, the chinrest support portion and base portion are made of one of: polyethylene, polypropylene, vinyl, nylon, rubber, leather, an impregnated material, a laminated fibrous material, a plasticized materials, cardboard and paper.

11. The system according to claim 1, wherein a first end of the shaft support portion and a second end of the shaft support portion are outwardly flared.

12. The system according to claim 1, wherein the upper-portion is molded to conform to the patient's chin.

13. The system according to claim 1, further comprising a point of contiguity where the lower portion of the chin support portion and a first end of the shaft support portion are coupled.

14. The system according to claim 13, wherein the chin support portion and shaft support portion are adjustable at the point of contiguity.

15. The system according to claim 1, wherein the shaft support portion is bendable.

16. A method of assisting in the maintenance of patency to a patient's airway, comprising:
    providing a malleable shaft support portion comprising a flexible material that will maintain its shape when bent;
    providing a malleable chinrest support portion comprising a flexible material that includes an upper portion including a concave inner area shaped to substantially surround a portion of the patient's chin received therein, and a lower portion coupled to, and extending towards, a first end of the shaft support portion; and
    providing a base portion comprising a malleable material including an upper portion coupled to a second end of the shaft support portion and a lower portion configured for stable positioning on a patient's manubrium;
    placing the base portion at the level of the patient's manubrium;
    positioning the patient's head in the sniffing position; and
    inserting the patient's chin in the chinrest support portion.

17. The method of claim 16, further comprising adjusting the shaft support portion and the chin rest support portion to maintain patency to the patient.

* * * * *